US008022698B2

(12) United States Patent
Rottengatter et al.

(10) Patent No.: US 8,022,698 B2
(45) Date of Patent: *Sep. 20, 2011

(54) JOINT COMPRESSION OF MULTIPLE ECHO TRAINS USING PRINCIPAL COMPONENT ANALYSIS AND INDEPENDENT COMPONENT ANALYSIS

(75) Inventors: Peter Rottengatter, Celle (DE); Mouin Hamdan, Celle (DE)

(73) Assignee: Baker Hughes Incorporated, Houston, TX (US)

( * ) Notice: Subject to any disclaimer, the term of this patent is extended or adjusted under 35 U.S.C. 154(b) by 176 days.

This patent is subject to a terminal disclaimer.

(21) Appl. No.: 12/347,784

(22) Filed: Dec. 31, 2008

(65) Prior Publication Data
US 2009/0174402 A1 Jul. 9, 2009

Related U.S. Application Data

(60) Provisional application No. 61/019,462, filed on Jan. 7, 2008, provisional application No. 61/028,067, filed on Feb. 12, 2008.

(51) Int. Cl.
*G01V 3/00* (2006.01)
*G01R 33/20* (2006.01)
(52) U.S. Cl. ........................ 324/303; 324/306; 324/314
(58) Field of Classification Search .......... 324/300–322; 702/11; 600/407–435
See application file for complete search history.

(56) References Cited

U.S. PATENT DOCUMENTS

| 5,291,137 | A | * | 3/1994 | Freedman | 324/303 |
|---|---|---|---|---|---|
| 5,381,092 | A | * | 1/1995 | Freedman | 324/303 |
| 5,486,762 | A | * | 1/1996 | Freedman et al. | 324/303 |
| 6,215,304 | B1 | | 4/2001 | Slade | |
| 6,686,736 | B2 | | 2/2004 | Schoen et al. | |
| 6,856,132 | B2 | * | 2/2005 | Appel et al. | 324/303 |
| 6,859,033 | B2 | * | 2/2005 | Speier | 324/303 |
| 7,495,436 | B2 | * | 2/2009 | Hamdan et al. | 324/303 |
| 7,821,260 | B2 | * | 10/2010 | Hamdan et al. | 324/303 |
| 2004/0041562 | A1 | * | 3/2004 | Speier | 324/303 |
| 2004/0090230 | A1 | * | 5/2004 | Appel et al. | 324/307 |
| 2004/0169511 | A1 | * | 9/2004 | Minh et al. | 324/303 |
| 2005/0206378 | A1 | * | 9/2005 | Hamdan et al. | 324/303 |
| 2006/0273788 | A1 | * | 12/2006 | Georgi et al. | 324/303 |
| 2008/0036457 | A1 | * | 2/2008 | Thern et al. | 324/303 |
| 2008/0183390 | A1 | * | 7/2008 | Hamdan et al. | 702/11 |
| 2009/0125239 | A1 | * | 5/2009 | Niemeyer et al. | 702/11 |
| 2009/0174402 | A1 | * | 7/2009 | Rottengatter et al. | 324/303 |
| 2009/0292473 | A1 | * | 11/2009 | Kruspe et al. | 702/8 |

OTHER PUBLICATIONS

Miller et al.; "Spin Echo Magnetic Resonance Logging: Porosity and Free Fluid Index Determination," SPE 20561, 65th Annual Technical Conference and Exhibition of the Society of Petroleum Engineers, New Orleans, LA, Sep. 23-26, 1990, pp. 321-334.

* cited by examiner

Primary Examiner — Melissa J Koval
Assistant Examiner — Tiffany A Fetzner
(74) Attorney, Agent, or Firm — Mossman Kumar & Tyler PC

(57) ABSTRACT

NMR spin echo signals are acquired downhole. Principal Component Analysis is used to represent the signals by a weighted combination of the principal components and these weights are telemetered to the surface. At the surface, the NMR spin echo signals are recovered and inverted to give formation properties.

16 Claims, 6 Drawing Sheets

JOINT COMPRESSION OF MULTIPLE ECHO TRAINS USING PRINCIPAL COMPONENT ANALYSIS AND INDEPENDENT COMPONENT ANALYSIS

CROSS-REFERENCES TO RELATED APPLICATIONS

This application claims priority from U.S. Provisional Patent Application Ser. No. 61/019,462 filed on Jan. 7, 2008 and from U.S. Provisional Patent Application Ser. No. 61/028,067 filed on Feb. 12, 2008.

BACKGROUND OF THE DISCLOSURE

1. Field of the Disclosure

The present disclosure relates generally to determining geological properties of subsurface formations using Nuclear Magnetic Resonance ("NMR") methods for logging wellbores, particularly for representing NMR echo trains by a limited number of functional parameters, enabling efficient transmission of echo train from a downhole location.

2. Description of the Related Art

NMR methods are among the most useful non-destructive techniques of material analysis. When hydrogen nuclei are placed in an applied static magnetic field, a small majority of spins are aligned with the applied field in the lower energy state, since the lower energy state in more stable than the higher energy state. The individual spins precess about the axis of the applied static magnetic field vector at a resonance frequency also termed as Larmor frequency. This frequency is characteristic to a particular nucleus and proportional to the applied static magnetic field. An alternating magnetic field at the resonance frequency in the Radio Frequency (RF) range, applied by a transmitting antenna to a subject or specimen in the static magnetic field transfers nuclear spins into a coherent superposition of the lower energy state and the higher energy state. In this superposition state the magnetization of the spins precesses about the axis of the static magnetic field vector and therefore induces an oscillating voltage in a receiver antenna even after the transmitted field is switched off, whose amplitude and rate of decay depend on the physicochemical properties of the material being examined. The applied RF field is designed to perturb the thermal equilibrium of the magnetized nuclear spins, and the time dependence of the emitted energy is determined by the manner in which this system of spins looses coherence and returns to equilibrium magnetization. The return is characterized by two parameters: $T_1$, the longitudinal or spin-lattice relaxation time; and $T_2$, the transverse or spin-spin relaxation time.

Measurements of NMR parameters of fluid filling the pore spaces of earth formations such as relaxation times of the hydrogen spins, diffusion coefficient and/or the hydrogen density is the basis for NMR well logging. NMR well logging instruments can be used for determining properties of earth formations including the fractional volume of pore space and the fractional volume of mobile fluid filling the pore spaces of the earth formations.

One basic problem encountered in NMR logging or MRI (imaging) is the vast amount of data that has to be analyzed. In well logging with wireline instruments, the downhole processing capabilities are limited as is the ability to transmit data to an uphole location for further analysis since all the data are typically sent up a wireline cable with limited bandwidth. In the so-called Measurement-while-drilling methods, the problem is exacerbated due to the harsh environment in which any downhole processor must operate and to the extremely limited telemetry capability: data are typically transmitted at a rate of no more than twenty bits per second.

A second problem encountered in NMR logging and MRI is that of analysis of the data. As will be discussed below, the problem of data compression and of data analysis are closely inter-related.

Methods of using NMR measurements for determining the fractional volume of pore space and the fractional volume of mobile fluid are described, for example, in *Spin Echo Magnetic Resonance Logging: Porosity and Free Fluid Index Determination*, M. N. Miller et al, Society of Petroleum Engineers paper no. 20561, Richardson, Tex., 1990. In porous media there is a significant difference in the $T_1$ and $T_2$ relaxation time spectra of the fluids mixture filling the pore space. Thus, for example, light hydrocarbons and gas may have $T_1$ relaxation time of about several seconds, while $T_2$ may be thousand times less. This phenomenon is due to diffusion effect in internal and external static magnetic field gradients. Internal magnetic field gradients are due to magnetic susceptibility difference between rock formation matrix and pore filling fluid.

Since oil is found in porous rock formations, the relationships between porous rocks and the fluids filling their pore spaces are extremely complicated and difficult to model. Nuclear magnetic resonance is sensitive to main petrophysical parameters, but has no capabilities to establish these complex relationships. Oil and water are generally found together in reservoir rocks. Since most reservoir rocks are hydrophilic, droplets of oil sit in the center of pores and are unaffected by the pore surface. The water-oil interface normally does not affect relaxation, therefore, the relaxation rate of oil is primarily proportional to its viscosity. However, such oil by itself is a very complex mixture of hydrocarbons that may be viewed as a broad spectrum of relaxation times. In a simple case of pure fluid in a single pore, there are two diffusion regimes that govern the relaxation rate. Rocks normally have a very broad distribution of pore sizes and fluid properties. Thus it is not surprising that magnetization decays of fluid in rock formations are non-exponential. The most commonly used method of analyzing relaxation data is to calculate a spectrum of relaxation times. The Carr-Purcell-Meiboom-Gill (CPMG) pulse sequence is used to determine the transverse magnetization decay. The non-exponential magnetization decays are fit to the multi-exponential form:

$$M(t) = \sum_{i=1}^{L} m(T_{2i}) e^{-t/T_{2i}} \quad (1)$$

where M(t) represents the spin echo amplitudes, equally spaced in time, and the $T_{2i}$ are predetermined time constants, equally spaced on a logarithm scale, typically between 0.3 ms and 3000 ms. The set of m are found using a regularized nonlinear least squares technique. The function $m(T_{2i})$, conventionally called a $T_2$ distribution, usually maps linearly to a volumetrically weighted distribution of pore sizes.

The calibration of this mapping is addressed in several publications. Prior art solutions seek a solution to the problem of mathematical modeling the received echo signals by the use of several techniques, including the use of non-linear regression analysis of the measurement signal and non-linear least square fit routines. Other prior art techniques include a variety of signal modeling techniques, such as polynomial rooting, singular value decomposition (SVD) and miscellaneous refinements thereof, to obtain a better approximation of the received signal. A problem with prior art signal compressions is that some information is lost.

Inversion methods discussed in prior art are generally computationally intensive and still end up with a large number of parameters that have to be transmitted uphole. In particular, no simple methods have been proposed to take advantage of prior knowledge about the structure of the investigated material and the signal-to-noise (SNR) ratio of the received echo signal. Also, no efficient solutions have been proposed to combine advanced mathematical models with simple signal processing algorithms to increase the accuracy and numerical stability of the parameter estimates. Finally, existing solutions require the use of significant computational power which makes the practical use of those methods inefficient, and frequently impossible to implement in real-time applications.

U.S. patent application Ser. No. 11/845,983 of Thern et al. discloses a method which includes conveying a nuclear magnetic resonance (NMR) sensing apparatus into a borehole, using the NMR sensing apparatus for obtaining a signal indicative of the property of the earth formation, using a predetermined matrix to estimate from the signal a parametric representation of the relaxation of nuclear spins in terms of at least one basis function, telemetering the parametric representation to a surface location and, at the surface location, using the telemetered parametric representation to estimate the property of the earth formation. The signal may be a spin echo signal and representation of relaxation of nuclear spins may include a transverse relaxation time ($T_2$) distribution. The at least one basis function may be a Gaussian function, and parametric representation may include a mean, a standard deviation, and an amplitude of the Gaussian function. Defining the predetermined matrix may be done by performing a regression analysis on synthetic NMR signals and/or NMR signals measured on samples having known properties. The dependent variable in the regression analysis may be a spin echo signal. The regression analysis may be a partial least-squares, a principal component regression, an inverse least-squares, a ridge regression, a Neural Network, a neural net partial least-squares regression, and/or a locally weighted regression. The determined property may be bound volume irreducible, effective porosity, bound water, clay-bound water, total porosity, a permeability, and/or a pore size distribution.

A potential drawback of the method of Thern is the lack of adaptability: the number of Gaussian functions used to characterize the $T_2$ distribution and the matrix are predefined and may not be equally suitable for all types of earth formations and all types of pulse sequences used in acquisition of the data. These drawbacks are addressed in the present disclosure.

SUMMARY OF THE DISCLOSURE

One embodiment of the disclosure is a method of determining a property of an earth formation. The method includes conveying a nuclear magnetic resonance (NMR) sensing apparatus into a borehole, using the NMR sensing apparatus for obtaining a signal indicative of the property of the earth formation, representing the NMR signals using a set of eigenfunctions and telemetering a representation of the NMR signals as a combination of the eigenfunctions to a surface location.

Another embodiment of the disclosure is an apparatus for determining a property of an earth formation. The apparatus includes a nuclear magnetic resonance (NMR) sensing apparatus configured to be conveyed into a borehole and obtain a signal indicative of the property of the earth formation. The apparatus also includes a downhole processor configured to represent the NMR signals using a set of eigenfunctions and telemeter a representation of the NMR signals as a combination of the eigenfunctions to a surface location.

Another embodiment of the disclosure is a computer-readable medium accessible to a processor. The computer-readable medium includes instructions which enable the processor to represent at least one signal obtained by an NMR sensing apparatus in a borehole representative of a property of an earth formation by a set of eigenfunctions; and telemeter a representation of the at least one signal as a combination of the eigenfunctions to a surface location.

BRIEF DESCRIPTION OF THE DRAWINGS

The present disclosure is best understood with reference to the accompanying figures in which like numerals refer to like elements and in which:

FIG. 5 B shows the results obtained from the joint compression of the trainlet and the echo train of FIG. 5A.

DETAILED DESCRIPTION OF THE DISCLOSURE

Figure 1:
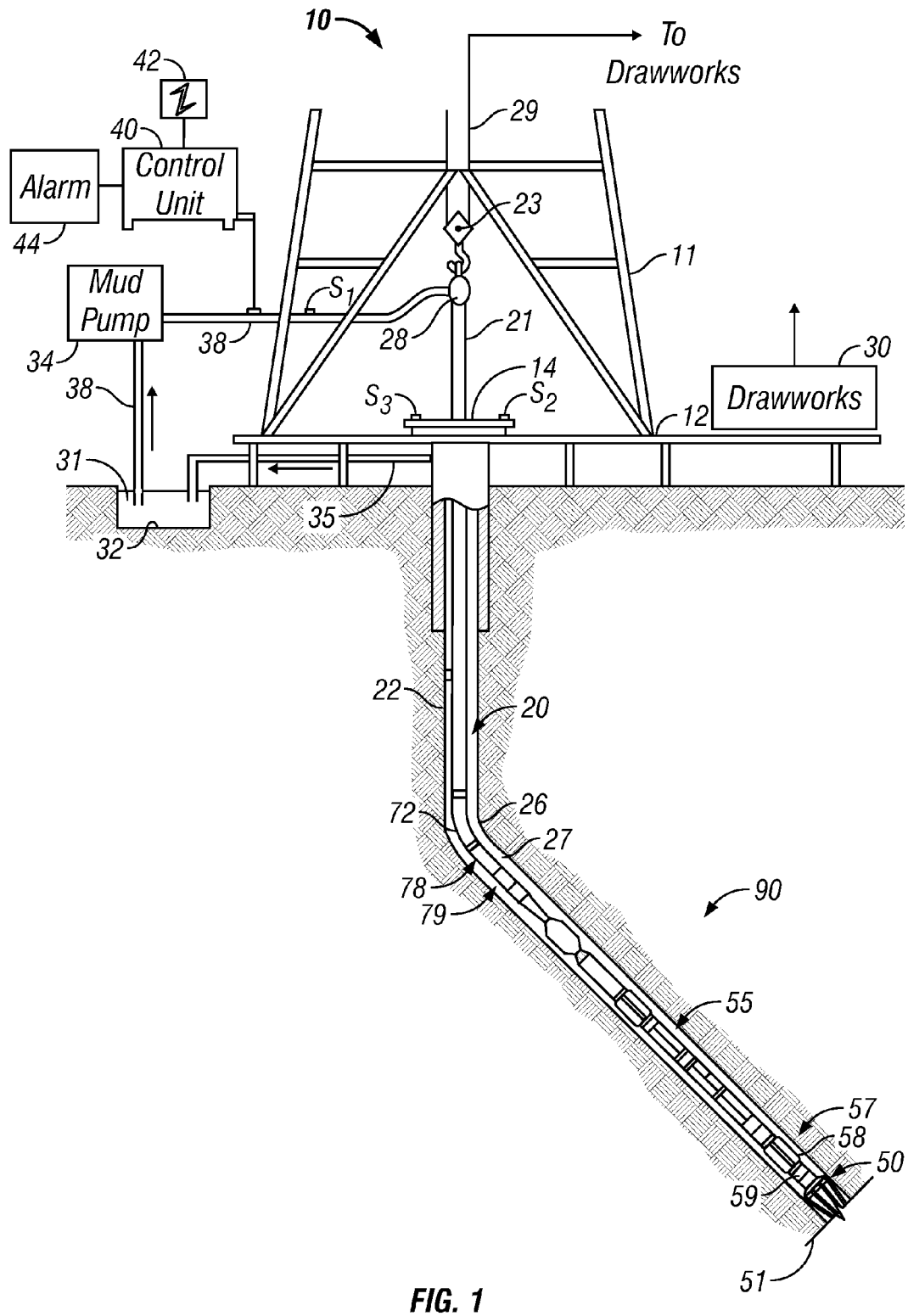
FIG. 1 shows a measurement-while-drilling tool suitable for use with the present disclosure.

FIG. 1 shows a schematic diagram of a drilling system 10 with a drillstring 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein. For the purposes of this disclosure, it is necessary to know the axial velocity (rate of penetration or ROP) of the bottomhole assembly. Depth information and ROP may be communicated downhole from a surface location. Alternatively, the method disclosed in U.S. Pat. No. 6,769,497 to Dubinsky et al. having the same assignee as the present application and the contents of which are incorporated herein by reference may be used. The method of Dubinsky uses axial accelerometers to determine the ROP. During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 38 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ typically placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the disclosure, the drill bit 50 is rotated by only rotating the drill pipe 22. In another embodiment of the disclosure, a downhole motor 55 (mud motor) is disposed in the drilling assembly 90 to rotate the drill bit 50 and the drill pipe 22 is rotated usually to supplement the rotational power, if required, and to effect changes in the drilling direction.

In an exemplary embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the disclosure, a drilling sensor module 59 is placed near the drill bit 50. The drilling sensor module contains sensors, circuitry and processing software and algorithms relating to the dynamic drilling parameters. Such parameters typically include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 typically includes a computer or a microprocessor-based processing system, memory for storing programs or models and data, a recorder for recording data, and other peripherals. The control unit 40 is typically adapted to activate alarms 44 when certain unsafe or undesirable operating conditions occur.

A suitable device for use of the present disclosure is disclosed in U.S. Pat. No. 6,215,304 to Slade, the contents of which are fully incorporated herein by reference. It should be noted that the device taught by Slade is for exemplary purposes only, and the method of the present disclosure may be used with many other NMR logging devices, and may be used for wireline as well as MWD applications.

Figure 2:
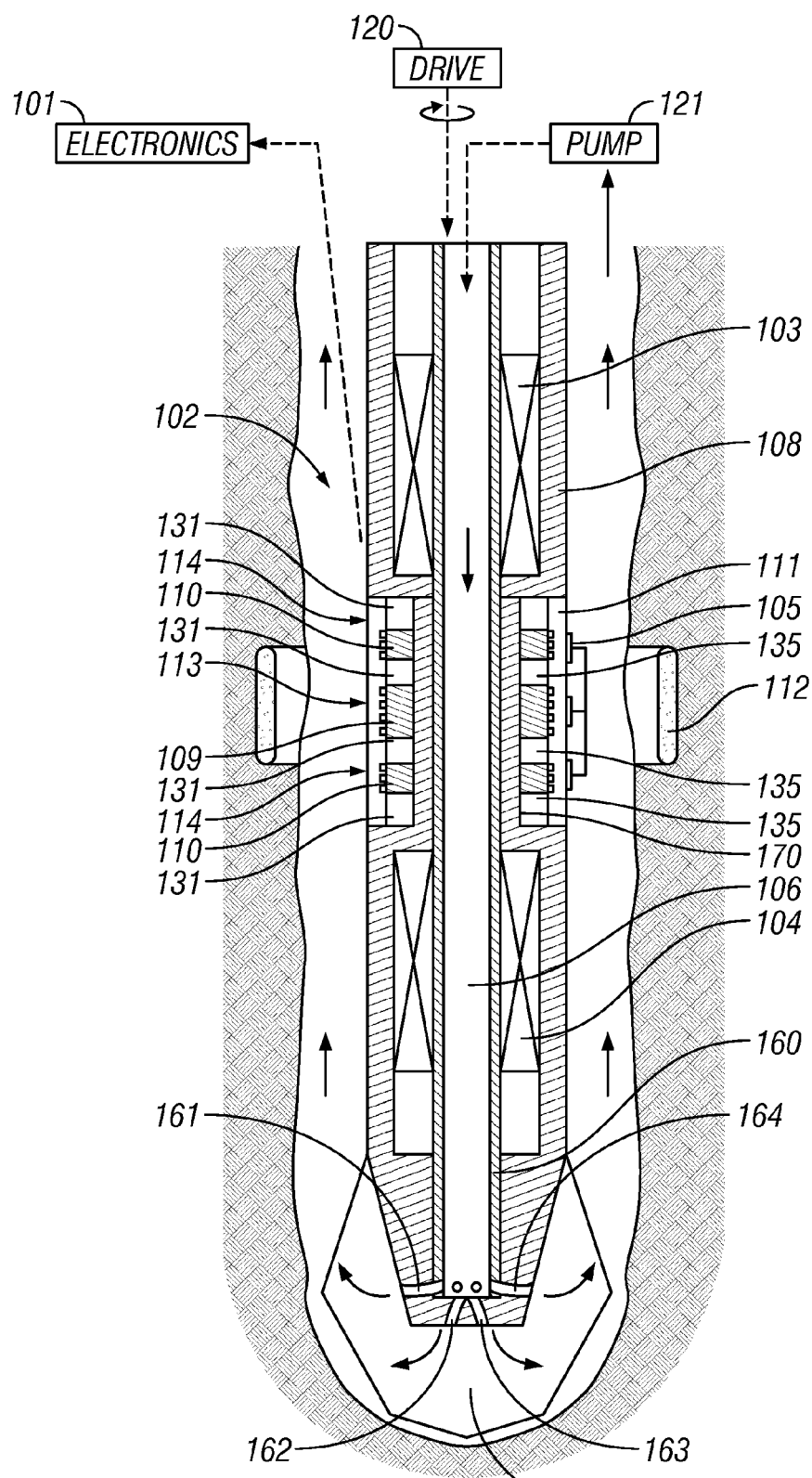
FIG. 2 (prior art) shows a sensor section of a measurement-while-drilling device suitable for use with the present disclosure.

Referring now to FIG. 2, the tool has a drill bit 107 at one end, a sensor section 102 behind the drill head, and electronics 101. The sensor section 102 comprises a magnetic field generating assembly for generating a Bo magnetic field (which is substantially time invariant over the duration of a measurement), and an RF system for transmitting and receiving RF magnetic pulses and echoes. The magnetic field generating assembly comprises a pair of axially spaced main magnets 103, 104 having opposed pole orientations (i.e. with like magnetic poles facing each other), and three ferrite members 109, 110 axially arranged between the magnets 103, 104. The ferrite members are made of "soft" ferrite which can be distinguished over "hard" ferrite by the shape of the BH curve which affects both intrinsic coercivity ($H_j$ the intersection with the H axis) and initial permeability ($\mu_i$, the gradient of the BH curve in the unmagnetized case). Soft ferrite $\mu_i$ values typically range from 10 to 10000 whereas hard ferrite has $\mu_i$, of about 1. Therefore the soft ferrite has large initial permeability (typically greater than 10, preferably greater than 1000). The RF system comprises a set of RF transmit antenna and RF receive antenna coil windings 105 arranged as a central "field forming" solenoid group 113 and a pair of outer "coupling control" solenoid groups 114.

The tool has a mud pipe 160 with a clear central bore 106 and a number of exit apertures 161-164 to carry drilling mud to the bit 107, and the main body of the tool is provided by a drill collar 108. Drilling mud is pumped down the mud pipe 160 by a pump 121 returning around the tool and the entire tool is rotated by a drive 120. Coiled tubing or a drillstring may be used for coupling the drive to the downhole assembly.

The drill collar 108 provides a recess 170 for RF transmit antenna and RF receive antenna coil windings 105. Gaps in the pockets between the soft ferrite members are filled with non-conducting material 131, 135 (e.g.: ceramic or high temperature plastic) and the RF coils 113, 114 are then wound over the soft ferrite members 109, 110. The soft ferrites 109, 110 and RF coil assembly 113, 114 are pressure impregnated with suitable high temperature, low viscosity epoxy resin (not shown) to harden the system against the effects of vibration, seal against drilling fluid at well pressure, and reduce the possibility of magnetoacoustic oscillations. The RF coils 113, 114 are then covered with wear plates 111 typically ceramic or other durable non-conducting material to protect them from the rock chippings flowing upwards past the tool in the borehole mud.

Because of the opposed magnet configuration, the device of Slade has an axisymmetric magnetic field and region of investigation 112 that is unaffected by tool rotation. Use of the ferrite results in a region of investigation that is close to the borehole. This is not a major problem on a MWD tool because there is little invasion of the formation by borehole drilling fluids prior to the logging. The region of investigation is within a shell with a radial thickness of about 20 mm and an axial length of about 50 mm. The gradient within the region of investigation is less than 2.7 G/cm. It is to be noted that these values are for the Slade device and, as noted above, the method of the present disclosure may also be used with other suitable NMR devices.

The method of the present disclosure is based on a representation of the acquired echo train of the earth formation as a weighted combination of principal components derived during data acquisition. This enables compression of the data: typically, instead of a thousand samples being required to depict a single echo train, 10 principal components are transmitted for each echo train. The principal components are derived downhole and may be transmitted uphole when previously derived principal components do not provide an adequate reconstruction of the echo trains downhole. At the surface, the received data (which may include adjective noise) is decompressed and inverted to give a $T_2$ distribution. We briefly discuss the Principal Component Analysis (PCA) method for compression and decompression of the data.

We represent a sequence of N echo trains, each M echoes long, by the matrix:

$$F = \begin{bmatrix} f_{1,1} & f_{1,2} & \cdots & \cdots & \cdots & \cdots & f_{1,M-1} & f_{1,M} \\ f_{2,1} & f_{2,2} & & & & & f_{2,M-1} & f_{2,M} \\ \vdots & \vdots & \ddots & & & & \vdots & \vdots \\ f_{N-1,1} & f_{N-1,2} & & \ddots & & & f_{N-1,M-1} & f_{N-1,M} \\ f_{N,1} & f_{N,2} & \cdots & \cdots & \cdots & & f_{N,M-1} & f_{N,M} \end{bmatrix} \quad (1)$$

Typically, the echo trains are 1000 samples long. The mean value of the j-th echo is denoted by:

$$\mu_j = \frac{1}{N} \sum_{i=1}^{N} f_{i,j}. \quad (2)$$

We next define the covariance matrix of the data by:

$$C = \frac{1}{M}[F'^T \cdot F'], \quad (3)$$

where $$F' = F - [\mu_1, \mu_2, \ldots \mu_{M-1}, \mu_M] \quad (4).$$

The covariance matrix C is decomposed into its eigenvalues and eigenvectors $$C = V\Lambda V^{-1} \quad (5),$$

where V is a matrix whose columns are the eigenvectors of C and $\Lambda$ is the diagonal matrix of eigenvalues:

$$\Lambda = \begin{bmatrix} \lambda_1 & 0 & \cdots & \cdots & 0 & 0 \\ 0 & \lambda_2 & & & 0 & 0 \\ \vdots & & \ddots & & & \vdots \\ \vdots & & & \ddots & & \vdots \\ 0 & 0 & & & \lambda_{M-1} & 0 \\ 0 & 0 & \cdots & \cdots & 0 & \lambda_M \end{bmatrix}, \quad (6)$$

with $\lambda_1 \geq \lambda_2 \geq \lambda_3 \ldots \geq \lambda_{M-1} \geq \lambda_M.$ (7)

With this ordering of the eigenvalues, the eigenvectors of V are the principal components.

The representation of the echo train data is done by the transformation $$\vec{M}' = V \cdot \vec{E} \quad (8),$$

and the inverse transform $$\vec{E} = V^{-1}\vec{M}' = V^T\vec{M}' \quad (9)$$

may be used to recover the data. Data compression is accomplished by truncating the matrix V to the first k rows corresponding to the dominant eigenvalues in eqn. (7). Table I shows an example of the dominant eigenvalues for an exemplary sequence of echo trains.

TABLE 1

Variance distribution

| Principal Component | Eigenvalue of Cov(F) | Value of this component | Cumulative variance |
|---|---|---|---|
| 1 | 214.0 | 94.3923 | 94.3923 |
| 2 | 10.7 | 4.7247 | 99.1171 |
| 3 | 1.57 | 0.6920 | 99.8091 |
| 4 | 0.327 | 0.1439 | 99.9530 |
| 5 | 0.0790 | 0.0348 | 99.9878 |
| 6 | 0.0203 | 0.0090 | 99.9968 |
| 7 | 0.00537 | 0.0024 | 99.9991 |
| 8 | 0.00142 | 0.0006 | 99.9998 |
| 9 | 0.000376 | 0.0002 | 99.9999 |
| 10 | 0.0000984 | 0.0000 | 100.0000 |
| 11 | 0.00002550 | 0.0000 | 100.0000 |
| 12 | 0.00000651 | 0.0000 | 100.0000 |
| 13 | 0.00000164 | 0.0000 | 100.0000 |
| 14 | 0.00000041 | 0.0000 | 100.0000 |
| 15 | 0.00000010 | 0.0000 | 100.0000 |

Figure 3:
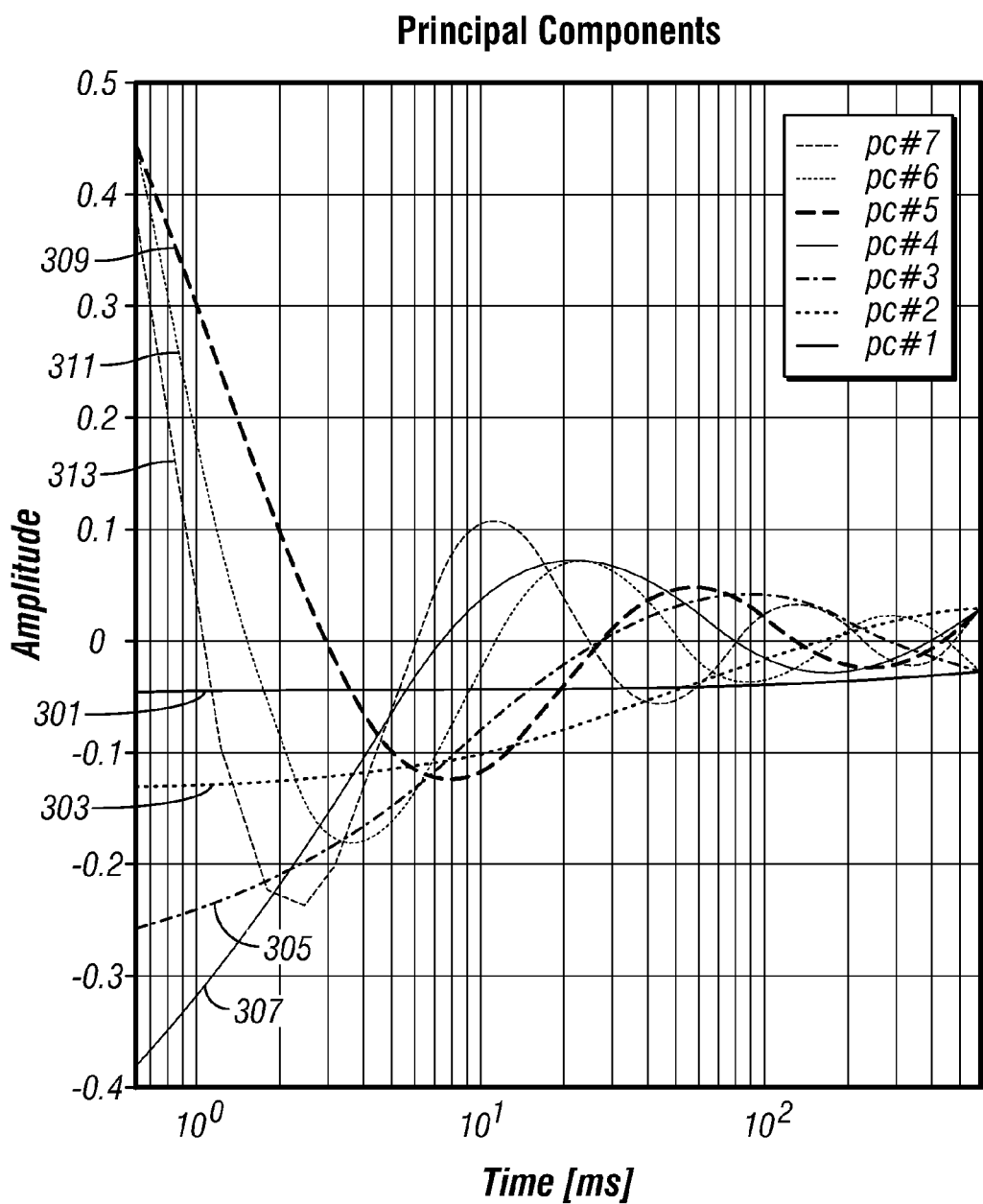
FIG. 3 shows exemplary principal component signals recovered from an ensemble of echo trains.

FIG. 3 shows the eigenvectors corresponding to the seven largest eigenvalues for the echo trains used in the derivation of Table I. They are ordered according to the magnitude of the eigenvalues 301, 303, 305, 307, 309, 311, 313.

Figure 4:
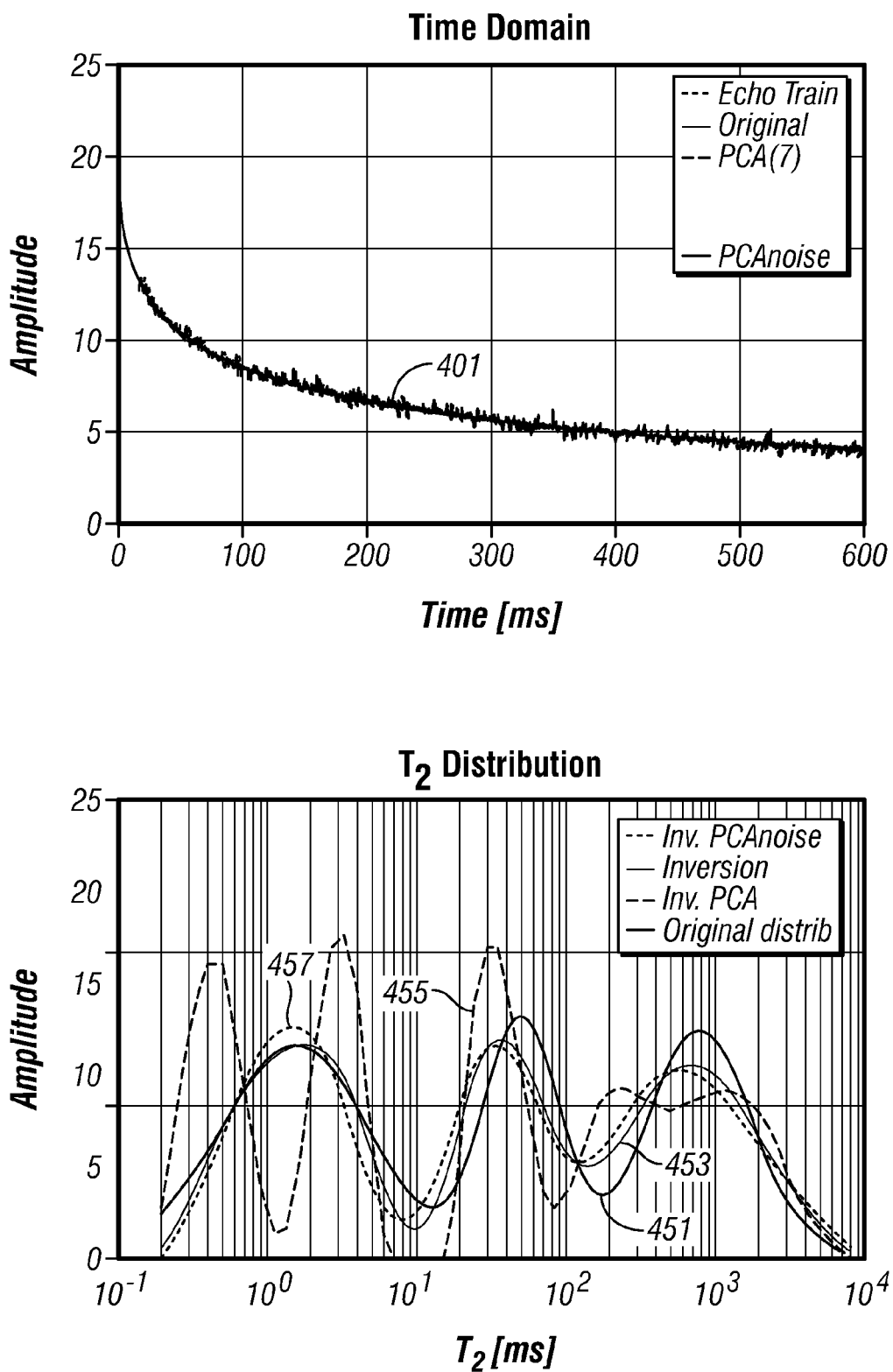
FIG. 4 shows (top): an exemplary echo train, and (bottom) comparison of an NMR $T_2$ with a reconstructed distribution.

In the lower part of FIG. 4, the curve 451 shows the original $T_2$ distribution corresponding to the noise free echo train. Using the curve 451, an original echo train (contained in 401 is generated). Noise is added to the original echo train to give a noisy echo train, also contained in 401 in the upper part of FIG. 4. The curve 453 is the result of inverting the noisy echo train. Comparison of 451 and 453 shows that even with a low level of noise, the inversion deviates from the correct result. Compressing and decompressing the noisy echo train gives a result that is still contained in 401. As discussed below, the results of the decompression are made up of the eigenvectors and are not multiexponential. Inverting the results of decompression gives the curve 455. Such a result is unsatisfactory because the inversion algorithm attempts to fit a multi-exponential to a curve that is not a multi-exponential any more. In order to avoid problems caused by the decompression results being non-exponential, a small amount of noise is added to the decompressed data before the inversion is carried out. When this noisy decompressed data is inverted, the result is shown by 457. Good agreement is seen between original $T_2$ distribution and the results of inversion using PCA.

Figure 5A:
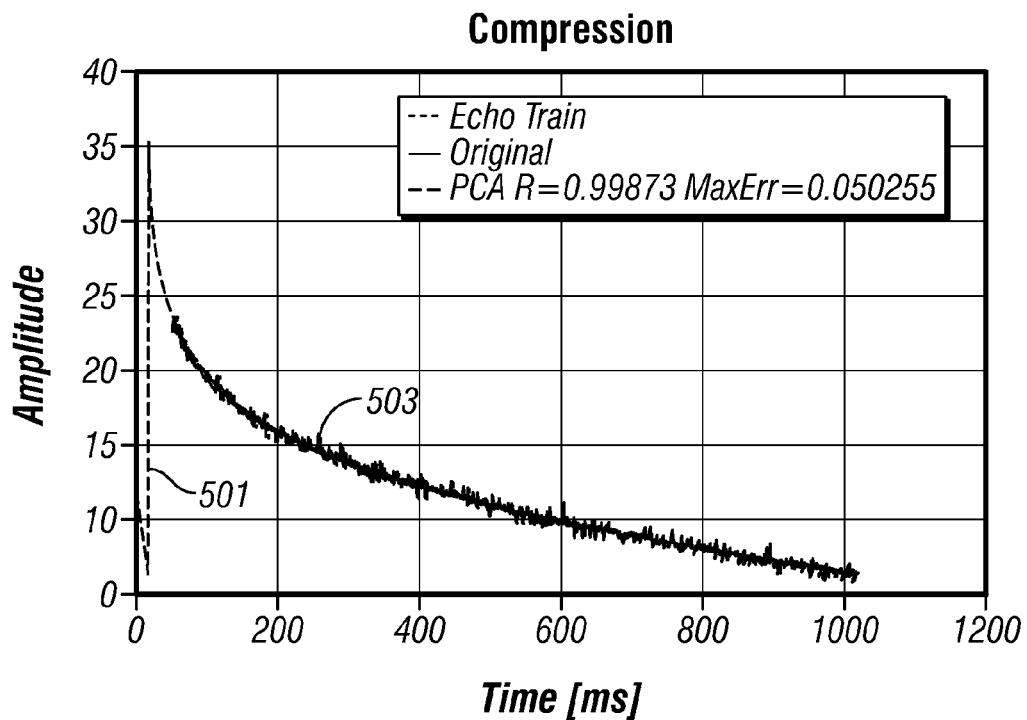
FIG. 5 A shows the concatenation of the trainlet and an echo train.
Figure 5B:
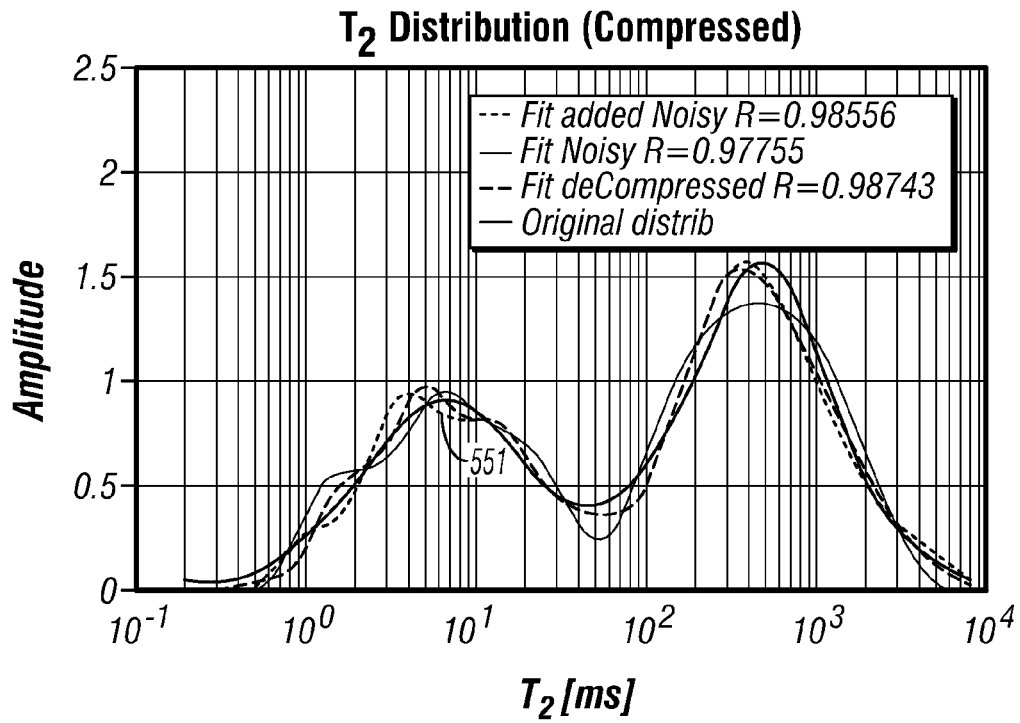

The PCA method may also be used to compress two or more echo trains in a single operation. The top portion of FIG. 5 shows a concatenation of two echo trains. The early portion 501 was acquired with a short wait time to get a measurement of rapidly relaxing components of the $T_2$ spectrum while the latter portion 503 is a long echo train intended to recover the slower components of the $T_2$ spectrum. The bottom portion of FIG. 5 shows little difference between the actual $T_2$ distribution and the results of using PCA on the concatenated echo trains.

It should be noted that the PCA also works for $T_1$ data. It has been found that joint compression of $T_1$ and $T_2$ data is satisfactory only for a fixed value of $T_1/T_2$. As this ratio is variable downhole, the joint compression of $T_1$ and $T_2$ data is of limited value.

Figure 6:
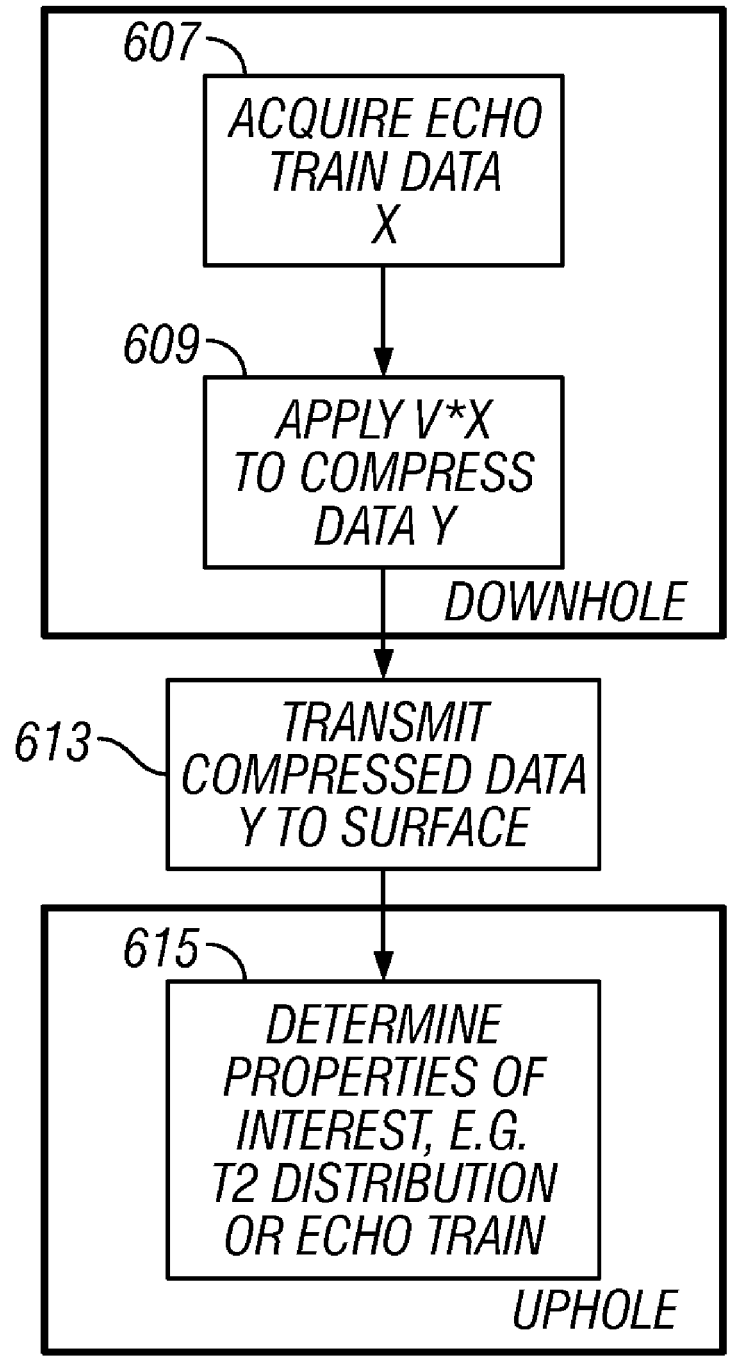
FIG. 6 is a flow chart showing further details of the implementation of the disclosure.

Turning now to FIG. 6, a flow chart summarizing the implementation of the method, including further details of the fitting method described above is shown. NMR data are acquired downhole 607. A truncated eigenvector matrix is applied 609 to the acquired echo train X. The compressed data are telemetered to the surface 613 and a reconstruction of the echo train is inverted to give the $T_2$ distribution 615.

In one embodiment of the disclosure, the eigenvector matrix is generated at the surface and the truncated matrix is loaded into the memory of the downhole processor. We create synthetic single-exponential data. This is a pure exponential function, 1000 values equally spaced by TE=0.6 ms, with given $T_2$. We create such a series of synthetic data values (a single exponential) for every value of $T_2$ that is to be considered, e.g. for 0.3 ms, 0.35 ms, . . . , 3000 ms. This gives 64 series of data values of single-exponentials. We note every conceivable measured echo train can be decomposed into a set of these series of data values. We therefore use PCA on this data to learn about its statistical properties. We want to do a coordinate system rotation (in a 1000 dimensional vector space), and we use PCA now to learn which basis vectors must be used in order to most economically express any multi-exponential in the new coordinate system. Note that while the original data matrix consisted of exponentials, after PCA, the eigenvectors are not necessarily exponentials. After the PCA is done, the matrix is truncated to the number of rows corresponding to the dominant eigenvalues. See eqn. (9).

In an alternate embodiment of the disclosure, the PCA is done downhole. This requires enormous computation power and is to be done sparingly in situations where it is established that a previously determined set of eigenvectors does not adequately represent the data. This may happen if, for example, parameters of the pulse sequence are changed, or if there is a major change in lithology and/or fluid content of the formation.

The recreation of properties of interest may cover $T_2$ distribution, volumetrics, permeability, echo trains, and other rock and fluid properties that are based on NMR data. It should further be noted that the method itself is of course not limited to downhole applications, As noted in Hamdan, bound volume irreducible, effective porosity, bound water, clay-bound water, and total porosity are among the formation properties that may be determined. From the $T_2$ relaxation spectrum, using an inversion method it is possible to estimate the pore-size distribution. The use of a pore-scale geometric model used in inverting NMR spectra is described, for example, in U.S. patent application Ser. No. 11/445,023 of Georgi et al., having the same assignee as the present disclosure and the contents of which are incorporated herein by reference. Determination of permeability is discussed in U.S. Pat. No. 6,686,736 to Schoen et al., having the same assignee as the present disclosure and the contents of which are incorporated herein by reference.

In an alternate embodiment of the disclosure, instead of principal component regression or principal component analysis (PCA), a method referred to as independent component analysis (ICA) may be used. In PCA, the basis vectors are obtained by solving the algebraic eigenvalue problem $$R^T(XX^T)R = \Lambda \quad (10)$$

where X is a data matrix whose columns are training samples (with the mean values removed), R is a matrix of eigenvectors, and $\Lambda$ is the corresponding diagonal matrix of eigenvalues. With such a representation, the projection of data, $C_n = R_n^T X$, from the original p dimensional space to a subspace spanned by n principal eigenvectors is optimal in the mean squared error sense. That is, the reprojection of $C_n$ back into the p dimensional space has minimum reconstruction error. In fact, if n is large enough to include all the eigenvectors with non-zero eigenvalues, the reprojection is lossless. The goal in PCA is to minimize the reconstruction error from compressed data.

In ICA, on the other hand the goal is to minimize the statistical dependence between the basis vectors. Mathematically, this can be written as $WX^T = U$, where ICA searches for a linear transformation W that minimizes the statistical dependence between the rows of U, given a training set X (as before). Unlike PCA, the basis vectors in ICA are neither orthogonal nor ranked in order. Also, there is no closed form expression to find W. Instead iterative algorithms have to be used. See Baek et al., PCA vs. ICA: A comparison on the FERET data set.

As noted by Baek, global properties are better represented by PCA while local structure is better represented by ICA. Based on a comparison of PCA to ICA, Baek concluded that for facial recognition problems (that are holistic in nature), PCA gave superior results. Baek further conjectured that evaluations on localized recognition tasks, such as recognizing facial expressions, ICA may give better results.

First and foremost, NMR measurements are indicative of the pore-size distribution in an earth formation. Secondarily, they are indicative of fluid types. By their very nature, the primary pore-size distribution in sedimentary rocks reflects the depositional energy, something that is episodic. Hence a significant amount of local structure is to be expected in the pore-size distribution. To put it another way, one would, for example, expect a high correlation between occurrences of pore-sizes of 1 μm and 1.01 μm: this would imply a local structure in the $T_2$ distribution and the $T_1$ distribution. In addition, the presence of heavy oil in a formation would also imply a local structure in the relaxation time distributions—once heavy oil has formed, it cannot be undone to light oil.

We next discuss implementation of ICA and differences with PCA. NMR relaxation of fluids in rocks exhibits multi-exponential behavior, which can be expressed in a discrete model as follows:

$$E(t) = \sum_j A_j e^{\left(\frac{t}{T_{2j}}\right)} \quad (11)$$

Assuming $T_{2j} = 0.2 \ldots 8192$ using increment of $2^{(1/4)}$, then $T_2$ will have a length of 64. This will translate into matrix notation when sampling the t at TE=0.6 μs and 1000 samples as:

$$E_{1 \times 1000} = A_{1 \times 64} \times F_{64 \times 1000} \quad (12),$$

where $A_j$ is proportional to the proton population of pores which have a relaxation time of $T_{2j}$, E(t) is the resultant echo-train in continuous time and E is discretized version of E(t). We first map all possible echo-trains with single exponential decay constant into a matrix F. Next, Through Independent Component Analysis we decompose the F matrix into 2 matrices.

$$F_{64 \times 1000} = M_{64 \times 64} S_{64 \times 1000} \quad (13)$$

F is a matrix that spans all single components decays in the echo train space.

S is a matrix of independent components (latent variables) of the corresponding type of acquisition (Created from ICA (Independent component analysis), using the fastICA algorithm, available with MATLAB, of the F matrix). M is the mixing matrix. Both M and S need to be estimated. Once S and M are found the manner of compressing data is as follows:

$$E_{1\times 1000} = A_{1\times 64} \times M_{64\times 64} \times S_{64\times 1000} \quad (14)$$

let $$Comp_{1\times 64} = A_{1\times 64} \times M_{64\times 64} \quad (14a)$$

Comp is called the Compression vector. Eqn. 4. can then be written into:

$$E_{1\times 1000} = Comp_{1\times 64} \times S_{64\times 1000} \quad (15)$$

Now multiply to the right both sides by inverse of $S \Rightarrow S^{-1}$.

$$E_{1\times 1000} \times S^{-1}_{1000\times 64} = Comp_{1\times 64} \times S_{64\times 1000} \times S^{-1}_{1000\times 64}$$

which leads to $$E_{1\times 1000} \times S^{-1}_{1000\times 64} = Comp_{1\times 64} \quad (16)$$

But the eigenanalysis of the Covariance of F tells us that beyond component 6 there will be almost zero percent of variance left as shown in Table 1.

Thus Eqn. 16 can be reduced into:

$$E_{1\times 1000} \times S^{-1}_{1000\times 6} = Comp_{1\times 6} \quad (17).$$

Eqn. 17 is applied in the downhole tool for compression of echo trains.

Eqn. 15 becomes Eqn. 18 and is applied in the surface system to decompress the mud-pulse-transmitted data:

$$E_{1\times 1000} = Comp_{1\times 6} \times S_{6\times 1000} \quad (18)$$

Eqn. 17 tells us that providing the inverse of a reduced form of the S matrix, we can compress an echo-train of length 1000, (and if we have an echo-train of length N, we need to create the S matrix of size 6×N,) into a 1×6 matrix. Furthermore Eqn. 18 tells us we could recover the echo-train by using the same model (independent components) and the corresponding compression.

The PCA algorithm differ from the ICA only in the way of decomposition Through Principal Component Analysis we decompose the F matrix into 2 matrices.

$$F_{64\times 1000} = Scores_{64\times 64} \times Loads_{64\times 1000} \quad (19),$$

Where F is a matrix that spans all single components decays, Loads is a matrix of eigenvectors of the corresponding type of acquisition (Created from Principal components decomposition of the F matrix) and scores are the eigenvalues of Matrix F. It is to be noted that Scores forms an orthogonal set ($Scores_i^T Scores_j = 0$ for $i \neq j$) and Loads forms an orthonormal set ($Loads_i^T Loads_j = 0$ for $i \neq j$ and $= 1$ for $i = j$) $\Rightarrow Loads^T = Loads^{-1}$. The scores $Scores_i$ of T is a linear combination of F defined by $Loads_i$ that is to say that $Scores_i$ is the projection of F on $Loads_i$. by replacing the value of F in Eqn. 10 into Eqn. 2

$$E_{1\times 1000} = A_{1\times 64} \times Scores_{64\times 64} \times Loads_{64\times 1000} \quad (20).$$

Let $$Comp_{1\times 64} = A_{1\times 64} \times Scores_{64\times 64} \quad (20a)$$

Comp is what we call a Compression vector. Eqn. 20a can then be written into:

$$E_{1\times 1000} = Comp_{1\times 64} \times Loads_{64\times 1000} \quad (21)$$

Now multiplying to the right by inverse of $Loads \Rightarrow Loads^{-1}$, and using the fact that $Loads^{-1} = Loads^T$ $$E_{1\times 1000} \times Loads^T_{1000\times 64} = Comp_{1\times 64} \times Loads_{64\times 1000} \times Loads^T_{1000\times 64}$$

which leads to $$E_{1\times 1000} \times Loads^T_{1000\times 64} = Comp_{1\times 64} \quad (22)$$

Eqn. 22 tells us that we could compress the whole Echo-Train from 1000 points into 64 points without losing any information. Analysis of PCA tells us that beyond component 5 there will be almost zero percent of variance left as the following table shows:

TABLE 2

Analysis of the variance contribution in each PCA component

| Principal Component | Eigenvalue of Cov(F) | Variance of this Component [%] | Variance of previous + this Component [%] |
|---|---|---|---|
| 1 | 214.0 | 94.3923 | 94.3923 |
| 2 | 10.70 | 4.7247 | 99.1171 |
| 3 | 1.57 | 0.6920 | 99.8091 |
| 4 | 0.327 | 0.1439 | 99.9530 |
| 5 | 0.0790 | 0.0348 | 99.9878 |
| 6 | 0.0203 | 0.0090 | 99.9968 |
| 7 | 0.00537 | 0.0024 | 99.9991 |
| 8 | 0.001420 | 0.0006 | 99.9998 |
| 9 | 0.000376 | 0.0002 | 99.9999 |
| 10 | 0.0000984 | 0.0000 | 100.0000 |
| 11 | 0.00002550 | 0.0000 | 100.0000 |
| 12 | 0.00000651 | 0.0000 | 100.0000 |
| 13 | 0.00000164 | 0.0000 | 100.0000 |
| 14 | 0.00000041 | 0.0000 | 100.0000 |
| 15 | 0.00000010 | 0.0000 | 100.0000 |

Thus Eqn. 22 can be reduced into:

$$E_{1\times 1000} \times Loads^T_{1000\times 5} = Comp_{1\times 5} \quad (23)$$

and Eqn. 21 becomes:

$$E_{1\times 1000} = Comp_{1\times 5} \times Loads_{5\times 1000} \quad (24)$$

Eqn. 23 tells us that providing a reduced form of the Loads matrix, we can compress an Echo-Train of length 1000, (and if we have an Echo-train of length N, we need to create the Loads matrix of size 5×N,) into 1×5 matrix. Furthermore Eqn. 24 tells us we could recover the echo-train by using the same model and the corresponding compression.

To summarize, the ICA algorithm can be basically be used as a replacement of the PCA.

Implicit in the control and processing of the data is the use of a computer program implemented on a suitable machine readable medium that enables the processor to perform the control and processing. The machine readable medium may include ROMs, EPROMs, EAROMs, Flash Memories and Optical disks.

What is claimed is:

1. A method of determining a property of an earth formation, the method comprising:
   conveying a nuclear magnetic resonance (NMR) sensing apparatus into a borehole;
   using the NMR sensing apparatus for obtaining at least two signals indicative of the property of the earth formation;
   representing a concatenation of the at least two signals using a set of eigenfunctions; and telemetering a representation of the at least two signals as a combination of the eigenfunctions to a surface location.

2. The method of claim 1 further comprising deriving the eigenfunctions using at least one of: (i) a principal component analysis, and (ii) an independent component analysis.

3. The method of claim 1 further comprising deriving the eigenfunctions at one of: (i) a surface location, and (ii) a downhole location.

4. The method of claim 1 wherein the at least two signals are selected from the group consisting of: (i) a spin echo signal representative of a transverse relaxation time ($T_2$) distribution, and (ii) a signal representative of the longitudinal relaxation time ($T_1$) distribution.

5. The method of claim 1 further comprising using the telemetered representation to provide an estimate the at least two signals and to estimate the property of the earth formation.

6. The method of claim 1 wherein the property is selected from the group consisting of: (i) bound volume irreducible, (ii) effective porosity, (iii) bound water, (iv) clay-bound water, (v) total porosity, (vi) a permeability, and (vii) a pore size distribution.

7. The method of claim 1 further comprising conveying the NMR sensing apparatus into the borehole on a bottomhole assembly using a drilling tubular.

8. An apparatus configured to determine a property of an earth formation, the apparatus comprising:
a nuclear magnetic resonance (NMR) sensing apparatus configured to be conveyed into a borehole and provide at least two signals indicative of the property of the earth formation; and
at least one processor configured to:
(A) represent the at least two signals using a set of eigenfunctions; and
(B) telemeter a representation of the at least two signals as a combination of the eigenfunctions to a surface location.

9. The apparatus of claim 8 further comprising a drilling tubular configured to convey the NMR sensing apparatus into the borehole on a bottomhole assembly.

10. The apparatus of claim 8 wherein the at least one processor is further configured to derive the eigenfunctions using at least one of: (i) a principal component analysis, and (ii) an independent component analysis.

11. The apparatus of claim 8 wherein the at least one processor is further configured to derive the eigenfunctions at one of: (i) a surface location, and (ii) a downhole location.

12. The apparatus of claim 8 wherein NMR sensing apparatus is further configured to provide the at least two signals selected from the group consisting of: (i) a spin echo signal representative of a transverse relaxation time ($T_2$) distribution, and (ii) a signal representative of the longitudinal relaxation time ($T_1$) distribution.

13. The apparatus of claim 8 further comprising a surface processor configured to use the telemetered representation to provide an estimate of the at least two signals and to estimate the property of the earth formation.

14. The apparatus of claim 8 wherein the NMR sensing apparatus is further configured to provide the at least two signals indicative of a property selected from the group consisting of: (i) bound volume irreducible, (ii) effective porosity, (iii) bound water, (iv) clay-bound water, (v) total porosity, (vi) a permeability, and (vii) a pore size distribution.

15. A non-transitory computer-readable medium having instructions that when read by a processor cause the processor to execute a method, the method comprising:
representing, by a set of eigenfunctions, a concatenation of at least two signals representative of a property of an earth formation obtained by an NMR sensing apparatus in a borehole and
telemetering a representation of the concatenation of the at least two signals as a combination of the eigenfunctions to a surface location.

16. The non-transitory computer-readable medium of claim 15 further comprising at least one of: (i) a ROM, (ii) an EPROM, (iii) an EAROM, (iv) a flash memory, and (v) an optical disk.

* * * * *